United States Patent
Salit et al.

(10) Patent No.: US 7,254,851 B2
(45) Date of Patent: Aug. 14, 2007

(54) PATIENT SUPPORT STRUCTURE HAVING A TABLETOP WITH A BREAST POSITIONING APERTURE FOR A LASER IMAGING APPARATUS

(75) Inventors: Emily Ann Salit, Cooper City, FL (US); David Marc Richter, Coral Springs, FL (US); Vicente Magraner, Miami, FL (US); Robert Henry Wake, Cooper City, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 91 days.

(21) Appl. No.: 10/292,619

(22) Filed: Nov. 13, 2002

(65) Prior Publication Data

US 2004/0092823 A1 May 13, 2004

(51) Int. Cl.
*A61B 5/05* (2006.01)

(52) U.S. Cl. .............................. 5/601; 5/735

(58) Field of Classification Search .................... 5/601, 5/613, 621, 632, 735 X, 930; 600/407, 445; 378/37, 209
See application file for complete search history.

(56) References Cited

U.S. PATENT DOCUMENTS

| 3,988,793 | A | | 11/1976 | Abitbol |
| 4,485,819 | A | * | 12/1984 | Igl .............................. 600/445 |
| 4,596,384 | A | | 6/1986 | Blosser |
| 5,078,142 | A | * | 1/1992 | Siczek et al. ............... 600/407 |
| 5,569,266 | A | | 10/1996 | Siczek |
| 5,692,511 | A | | 12/1997 | Grable |
| 5,876,339 | A | | 3/1999 | Lemire |
| 5,999,842 | A | | 12/1999 | Harrison et al. |
| 6,100,520 | A | * | 8/2000 | Wake et al. ................ 250/239 |
| 6,419,390 | B1 | | 7/2002 | Landis-Lowell |
| 6,480,281 | B1 | | 11/2002 | Van Der Mark et al. |
| 2005/0055774 | A1 | | 3/2005 | Marin et al. |

FOREIGN PATENT DOCUMENTS

DE 10026792 12/2001

\* cited by examiner

*Primary Examiner*—Patricia Engle
*Assistant Examiner*—Fredrick Conley
(74) *Attorney, Agent, or Firm*—Shlesinger, Arkwright & Garvey LLP

(57) ABSTRACT

A patient support structure for a laser imaging apparatus, comprises a tabletop to support a female patient in front-down, prone position. The tabletop includes an opening adapted to permit a breast of the patient to be vertically pendant below the tabletop. The opening is non-symmetric with respect to an axis of rotation of a scanning mechanism disposed below the tabletop.

20 Claims, 10 Drawing Sheets

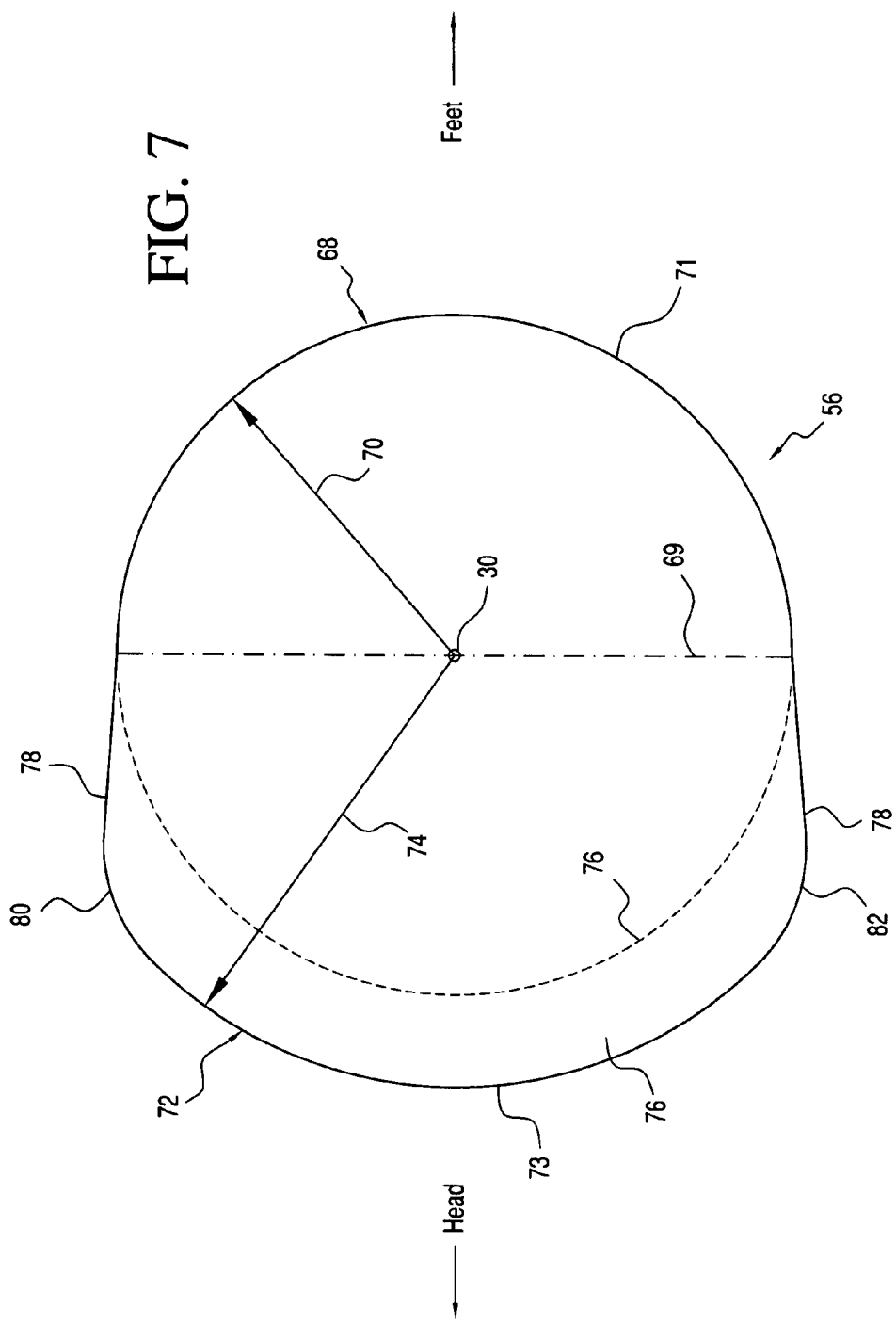

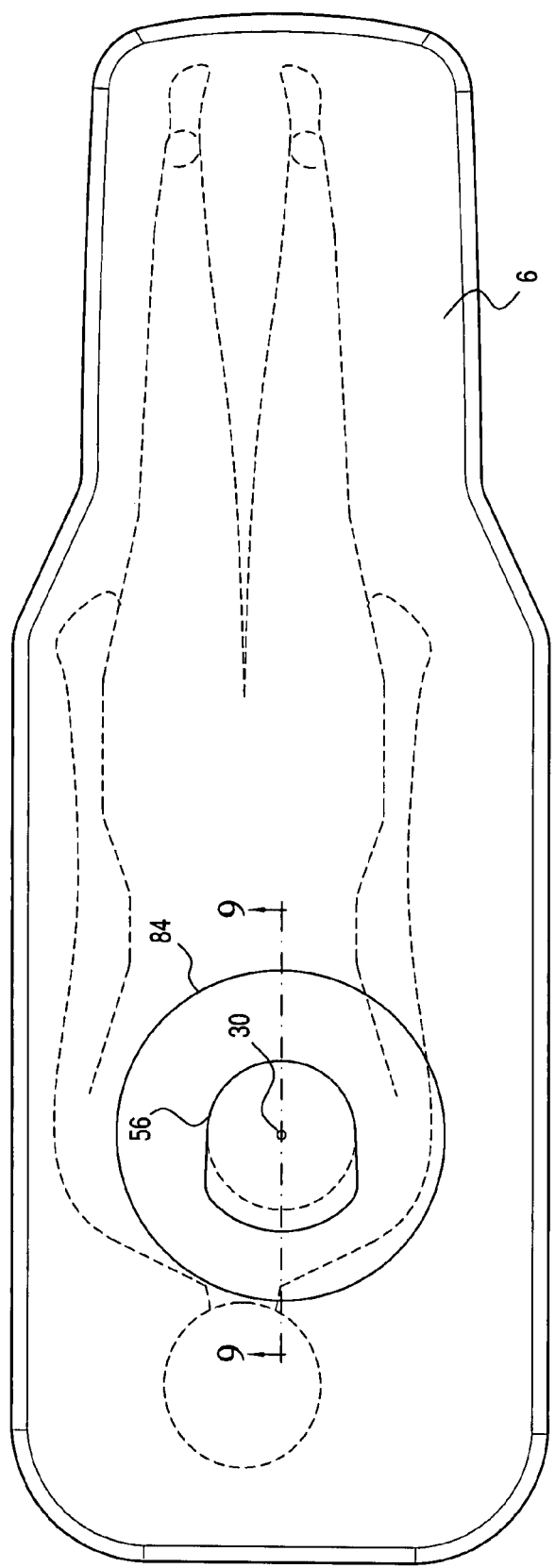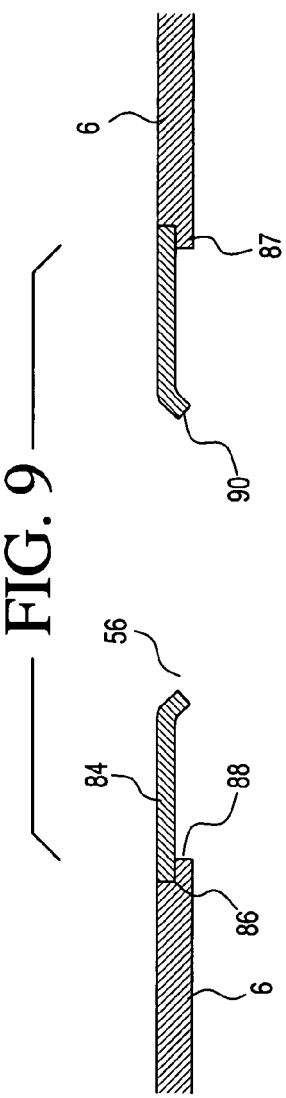

US 7,254,851 B2

PATIENT SUPPORT STRUCTURE HAVING A TABLETOP WITH A BREAST POSITIONING APERTURE FOR A LASER IMAGING APPARATUS

FIELD OF THE INVENTION

The invention relates generally to a diagnostic medical imaging apparatus that employs a near-infrared laser as a radiation source and particularly to a patient support structure having a tabletop with a breast positioning aperture to support a patient in a front-down prone position with her breast disposed vertically pendant in the aperture for scanning.

BACKGROUND OF THE INVENTION

In recent times, the use of light and more specifically laser light to noninvasively peer inside the body to reveal the interior structure has been investigated. This technique is called optical imaging. Optical imaging and spectroscopy are key components of optical tomography. Rapid progress over the past decade has brought optical computed tomography to the brink of clinical usefulness.

In optical tomography, the process of acquiring the data that will ultimately be used for image reconstruction is the first important step. Light photon propagation is not straight-line and techniques to produce cross-section images are mathematically intensive. To achieve adequate spatial resolution, multiple sensors are employed to measure photon flux density at small patches on the surface of the scanned object. The volume of an average female breast results in the requirement that data must be acquired from a large number of patches. The photon beam attenuation induced by breast tissue reduces the available photon flux to an extremely low level and requires sophisticated techniques to capture the low level signals.

U.S. Pat. No. 5,692,511 discloses such a laser imaging apparatus, This apparatus supports a patient in a face-down, prone position on a horizontal surface with a breast vertically pendant through an opening in a table surface. The patient's breast is pendant within a scanning chamber surrounded by an array of detectors, which revolve around the centerline of the scanning chamber. The array of detectors forms a portion of a circle and the scanning chamber and the opening or aperture in the tabletop are therefore circular. Provision is made to accommodate breasts of differing sizes via interchangeable breast centering rings, which provide circular openings or apertures of differing diameters, all centered on the centerline of the scanning chamber.

In such a computed-tomography geometry, it is required that the rotational centerline of the scanning mechanism pass through the object being scanned. Otherwise the laser beam does not impinge upon the object, and no optical transmission data can be obtained. While this constraint is easily met when the scanner is high in the breast, near the chest wall, the breast will likely move off the rotational centerline, as the scan progresses down the breast toward the nipple. Breasts are generally not conical in shape, typically being quite asymmetric from top to bottom, and somewhat asymmetric from left to right. Typically, even with a prone patient, the breast extends further above the nipple than below. The sagging caused by gravity is permanent, even in the prone position.

OBJECTS AND SUMMARY OF THE INVENTION

It is an object of the present invention to provide a non-circular opening in the tabletop of the (prone) patient support structure such that more of the patient's breast will remain on the rotational centerline of the sensors and radiation beam.

It is another object of the present invention to provide a method for positioning a patient's breast vertically pendant below a tabletop and disposed within a scanning chamber below the tabletop having a scanning mechanism rotating about vertical axis of rotation such that the lowest portion of the breast intersects with the axis of rotation of the scanning mechanism.

It is still another object of the present invention to provide a scanning apparatus, comprising a support structure including a tabletop to support a female patient in front-down, prone position with an opening in which a breast of the patient is vertically pendant below the tabletop and a detector array that rotates around the breast about a vertical axis disposed asymmetrically through the opening such that the axis intersects a bottom portion of the pendant breast.

In summary, the present invention provides a patient support structure for a laser imaging apparatus, comprising a tabletop to support a female patient in front-down, prone position. The tabletop includes an opening adapted to permit a breast of the patient to be vertically pendant below the tabletop. The opening is non-symmetric with respect to an axis of rotation of a scanning mechanism disposed below the tabletop.

The present invention also provides a method for positioning a patient's breast vertically pendant below a tabletop and disposed within a scanning chamber below the tabletop having a scanning mechanism rotating about vertical axis of rotation. The method comprises positioning the breast within the scanning chamber such that its lowest portion intersects with the axis of rotation of the scanning mechanism.

The present invention further provides a scanning apparatus, comprising a support structure including a tabletop to support a female patient in front-down, prone position. The tabletop has an opening adapted to permit a breast of the patient to be vertically pendant below the tabletop. A detector array to image the internal structure of the breast is disposed below the tabletop and includes a laser beam directed toward the breast and a plurality of detectors disposed in an arc around the opening to detect the laser beam after passage through the breast. The detector array is rotatable about a vertical axis disposed asymmetrically through the opening such that the axis intersects a bottom portion of the pendant breast.

These and other objects of the present invention will become apparent from the following detailed description.

BRIEF DESCRIPTIONS OF THE DRAWINGS

FIG. 7 shows a detailed view of the asymmetric and non-circular aperture of FIG. 5.

FIG. 8 is a schematic top view of the scanning apparatus of FIG. 1, showing a non-circular scanning aperture disposed in a removable centering disk.

FIG. 9 is schematic cross-sectional view along line 9-9 of FIG. 8.

DETAILED DESCRIPTION OF THE INVENTION

Figure 1:
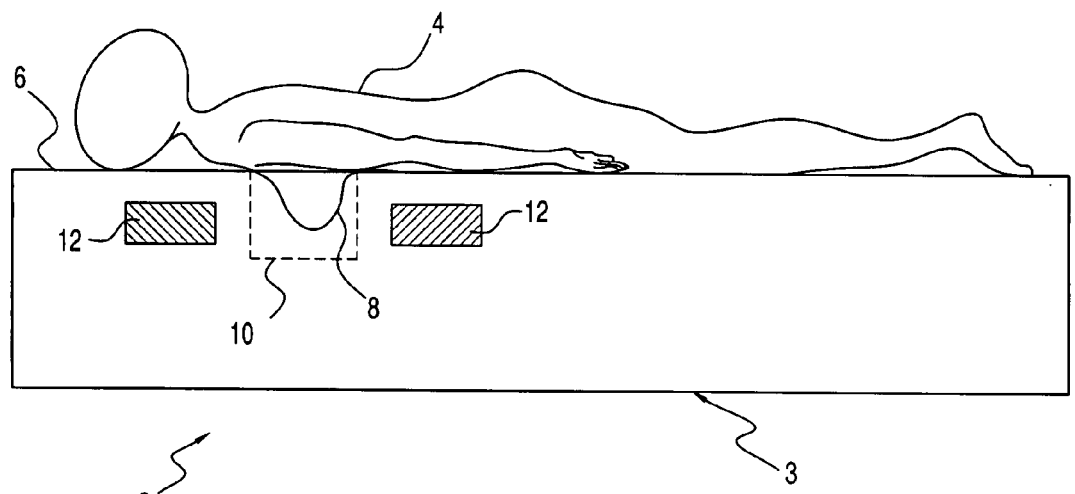
FIG. 1 is a schematic side elevational view of a scanning apparatus with a planar detector array, showing a prone patient positioned for optical tomographic study, with one breast pendant through a scanning aperture and disposed within the scanning chamber.

Referring to FIG. 1, a scanning apparatus 2, as described in U.S. Pat. Nos. 5,692,511 and 6,100,520, supports a prone patient 4 face down on a support structure 3 having an essentially flat tabletop 6. The patient's breast 8 is pendant within a scanning chamber 10, around which orbits a planar detector array 12. The planar detector array 12 orbits typically 360° around the vertical axis of the scanning chamber 10 and increments vertically downward between orbits to image successive slice planes of the breast. This is repeated until all the slice planes of the breast have been scanned.

Figure 2:
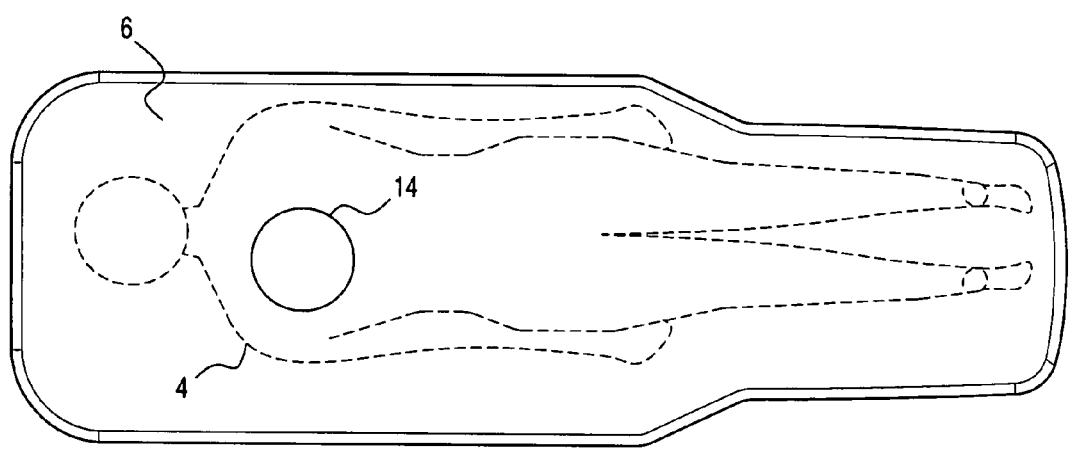
FIG. 2 is a schematic top view of the scanning apparatus of FIG. 1, showing a circular scanning aperture.

Referring to FIG. 2, a top view of the scanning apparatus 2 from FIG. 1 is shown. The patient 4 lies on the tabletop 6 with her breast through a circular scanning aperture 14. The patient is shown positioned for a scan of her left breast and would move to her left for a scan of her right breast.

Figure 3:
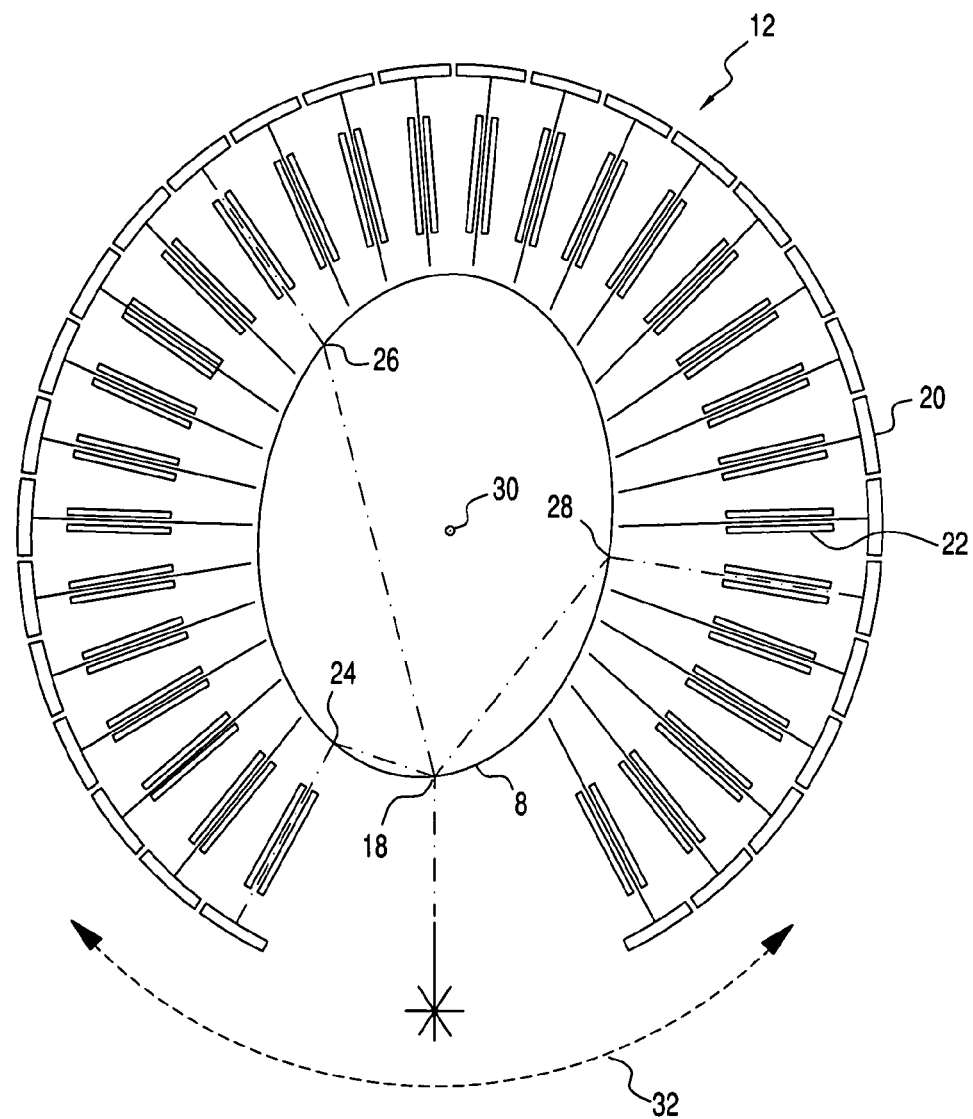
FIG. 3 is a schematic top view of the scanning chamber of FIG. 1, showing the planar detector array, consisting of a plurality of detectors disposed around an object being scanned and a laser light source.

Referring to FIG. 3, a top view of the planar detector array 12 is shown. The laser source 16 impinges on the scanned breast 8 at point 18. A plurality of detectors 20 defines an arc surrounding the breast. A collimator 22 defines each detector's field of view to a small area on the surface of the breast. Light enters the scanned object at point 18 and exits at every point on its circumference, such as at exit points 24, 26 and 28 corresponding to three detectors. The entire mechanism rotates, as indicated by the curved arrow 32.

Every detector 20 is collimated, aiming at the center of orbit rotation 30 and the laser source 16 also points toward the center of rotation. The detectors 20 are spaced at equal angular increments around the center of rotation. The orbit rotation is alternately 360° clockwise for one (horizontal) slice plane, then 360° counterclockwise for the next slice plane.

Figure 4A:
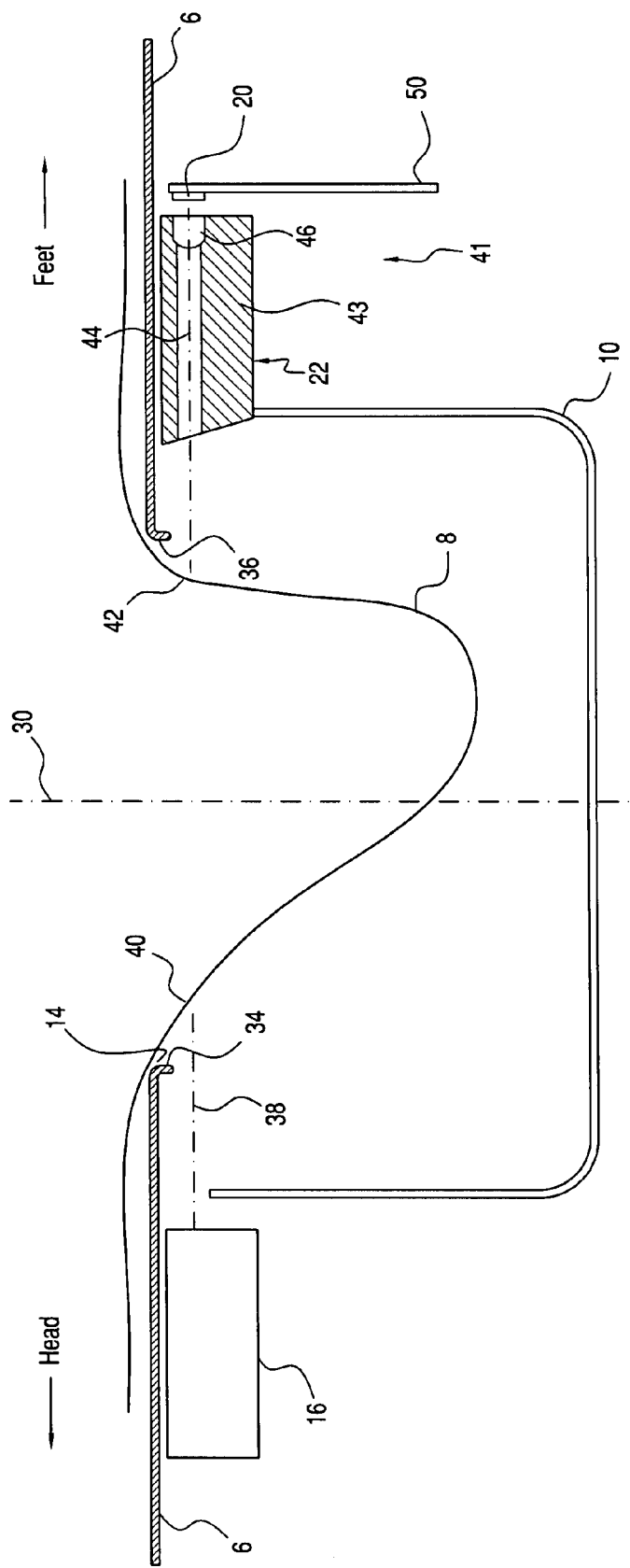
FIGS. 4A and 4B are schematic cross-sectional views through the planar detector array of FIG. 3, showing the laser light source and detectors and the breast pendant in the scanning chamber through a circular scanning aperture, with the scanning plane at two different positions on the breast.

Referring to FIG. 4A, a vertical cross-section through the planar detector array of FIG. 3 is shown. The planar detector array 12 is shown as imaging one slice, though any number of slices can be imaged simultaneously as disclosed in U.S. Pat. No. 6,100,520. The patient's breast 8 is pendant within the scanning chamber 10, with the rotational centerline 30. The patient is supported by the tabletop 6. The circular scanning aperture 14 in the tabletop 6, defined by points 34 and 36, is shown as symmetric about the rotational centerline 30. The laser source 16 projects a coherent light beam 38 which impinges on the patient's breast 8 at point 40. A detector assembly 41 (one of a plurality as shown in FIG. 3) receives the light emitted from the patient's breast at 42. The detector assembly consists of the collimator 22, shown as an opaque body 43 with a collimating channel 44. The collimating channel can be round, square, hexagonal, triangular or any other cross-sectional shape. The collimator restricts the field of view of each detector assembly to a small, defined area on the surface of the scanned breast. At the rear of each collimating channel is a lens 46, which focuses the light propagating down the collimating channel onto the photodetector 20. The lenses are shown as plano-convex, but could be biconvex or could be eliminated if the photodetector's area were larger than the collimating channel's area. The photodetector is connected to a signal processing electronics board 32, which would typically provide amplification and analog-to-digital conversion.

The laser source 16 could be a semiconductor diode laser, a solid-state laser or some other near-infrared light source. The photodetectors 20 could be photodiodes, avalanche photodiodes, phototransistors, photomultiplier tubes, microchannel plates or some other photosensitive device that converts incoming light photons to an electrical signal.

Figure 4B:
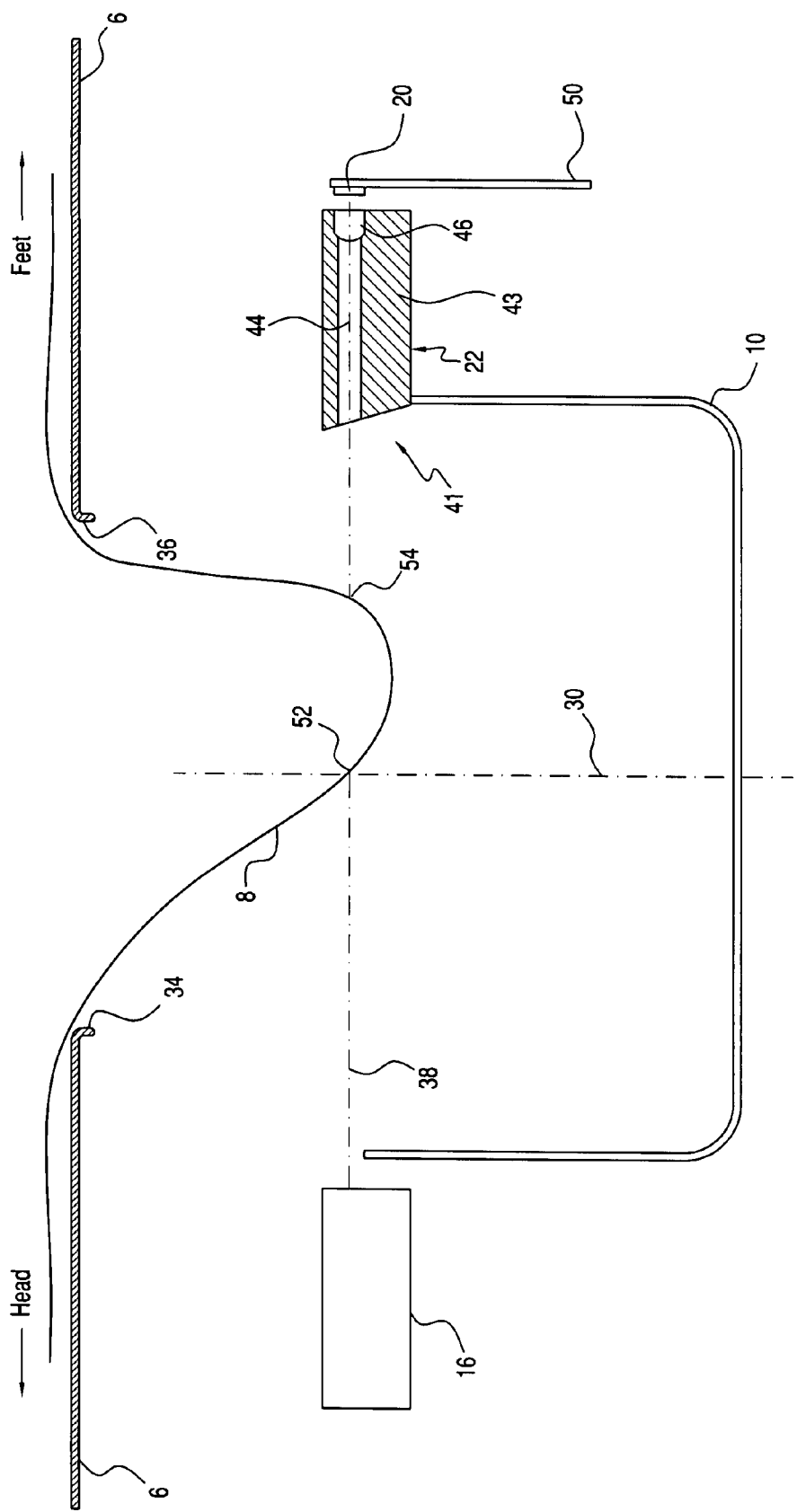

The detector assembly 41 is shown in FIG. 4A to be positioned at its highest point, nearest the patient's chest wall. The slice plane, defined by points 40 and 42, is as high as possible, the nominal starting point of the scan. Referring to FIG. 4B, the same detector assembly 41 is shown later in the scan, having moved downward, away from the chest wall. The laser source 16 is fixed relative to the detector assembly 41, such that it moves with the detector assembly during rotation around the breast and when it increments vertically. In other words, the laser source 16 or the laser beam 38 moves synchronously with the detector assembly 41 vertically and around the breast.

Because of the asymmetry of the breast, the laser beam 38 will miss the breast 8 entirely at some portion of the 360° orbit, as shown in FIG. 4B. The slice data is only valid if the laser beam 38 contacts the breast during the entire 360° orbit. At the level of the slice plane, defined by points 52 and 54, the rotational centerline 30 of the scanning chamber 10 no longer passes through the breast 8, which means that the laser beam 38 will not pass through the breast at some point in the rotation of the laser source 16 and the detector assembly 41. The scan cannot continue any lower on the breast as a consequence, since the scan is programmed to shut down when the beam 38 impinges on the detector 20 without passing through the breast.

Figure 5:
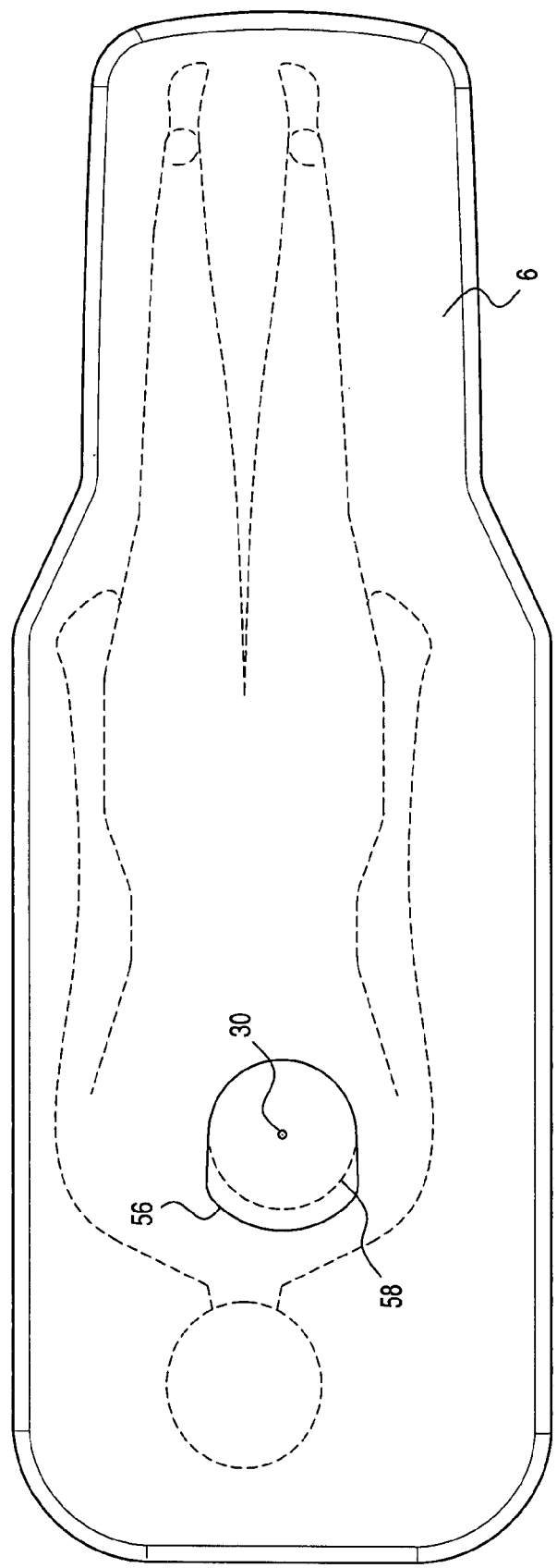
FIG. 5 is a schematic top view of the scanning apparatus of FIG. 1, showing a non-circular scanning aperture superimposed over the circular scanning aperture of FIG. 2.

A top view of the scanning apparatus 2 is shown in FIG. 5 with an asymmetric non-circular scanning aperture 56 in the tabletop 6. The aperture 56 is disposed non-symmetrically with respect to the axis of rotation 30 to provide more space on the side of the rotational centerline 30 toward the patient's head as compared to the circular aperture 14 (see FIG. 2). Part of the original circular aperture 14 is shown with a dashed line 58.

Figure 6A:
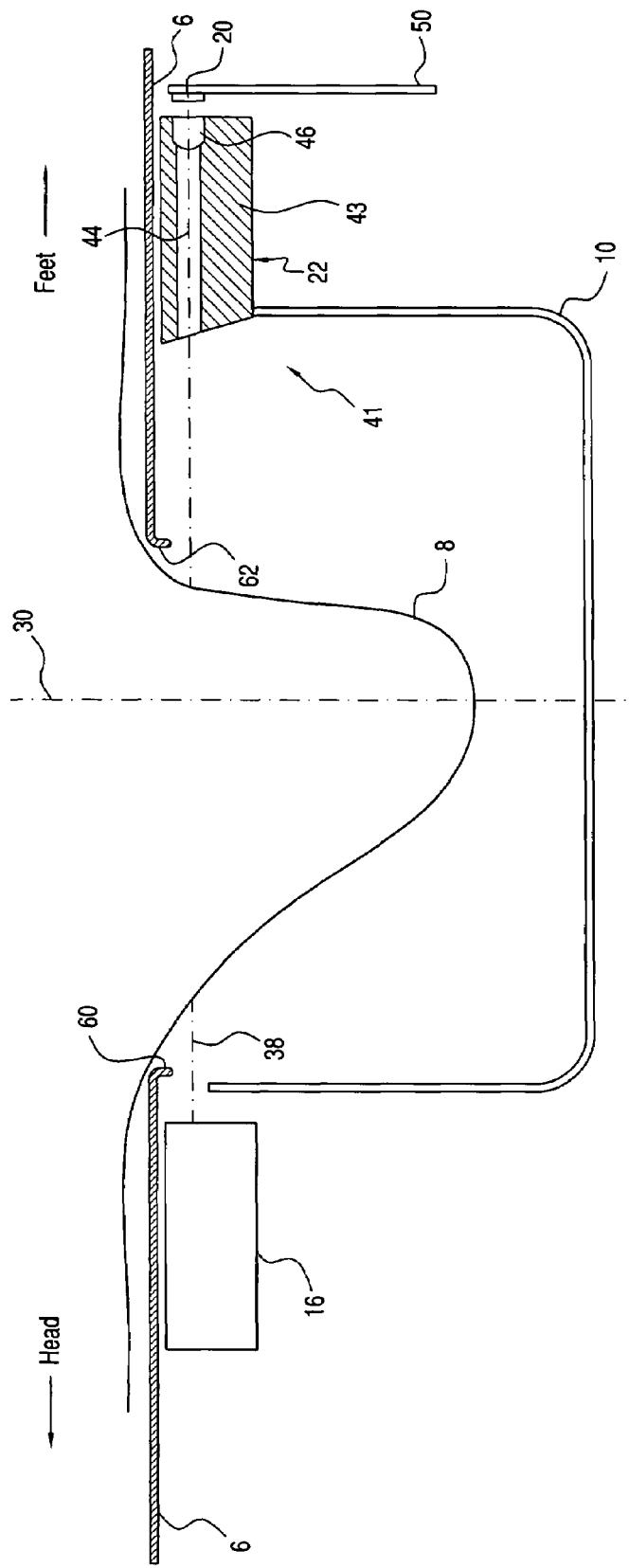
FIGS. 6A and 6B are schematic cross-sectional views through the planar detector array of FIG. 3, showing the laser light source and detectors and a breast pendant in the scanning chamber through the non-circular scanning aperture of FIG. 5, with the scanning plane at two different positions on the breast.
Figure 6B:
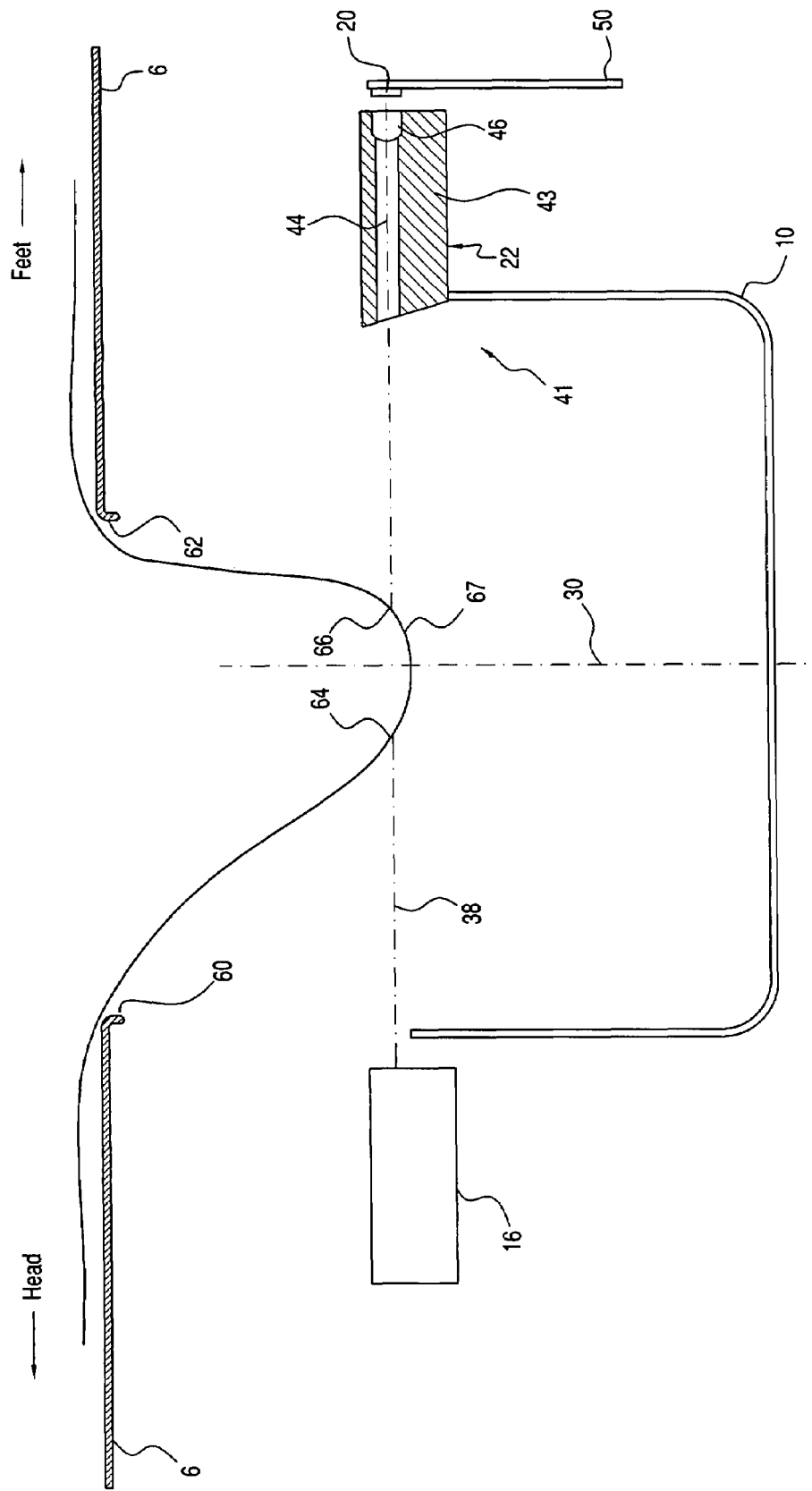

The detector assembly 41 positioned at its highest point, nearest the patient's chest wall, is shown in FIG. 6A. The asymmetric scanning aperture 56, defined by points 60 and 62, allows more space above the rotational centerline 30 of the scanning chamber 10 for the breast 8 toward the patient's head. In FIG. 6B, the detector assembly 41 and the laser source 16 have moved downward and the rotational centerline 30 is still within the breast, which means that the slice data is valid. The laser beam 38 impinges the breast at points 64 and 66, thereby still allowing the laser beam to penetrate the breast, as compared to FIG. 4B where the laser beam would not pass through the breast at some point in the orbit of the detector assembly. The asymmetric scanning aperture 56 permits the axis of rotation 30 to pass through the lowest portion 67 of the breast, thereby allowing the laser beam 38 not to miss the lower portion of the vertically pendant breast.

The preferred embodiment of the asymmetric scanning aperture 56 is shown in greater detail in FIG. 7. The scanning aperture 56 is defined with respect to the rotational centerline 30. An inferior portion 68 is bounded on one side of an imaginary line 69 extending across the aperture and intersecting the axis of rotation 30 and a peripheral edge 71 of the aperture extending toward the patient's feet. The inferior portion has a radius 70. A superior portion 72 is bounded by the opposite side of the imaginary line 69 and peripheral edge 73 extending from the imaginary line 69 toward the patient's head. The superior portion 72 has a radius 74 greater than the radius 70. The dotted line 76 shows the continuation of the radius 70 to illustrate the additional space 76 provided by the superior portion 72 of the aperture as compared to the circular aperture 14. The two radii are connected by tangents 78 to radius 70 with fillets 80 and 82 at the intersections of the tangents 78 with the radius 74. The inferior portion 68 is seen to semi-circular, while the superior portion 72 includes a circular arc.

Figure 10:
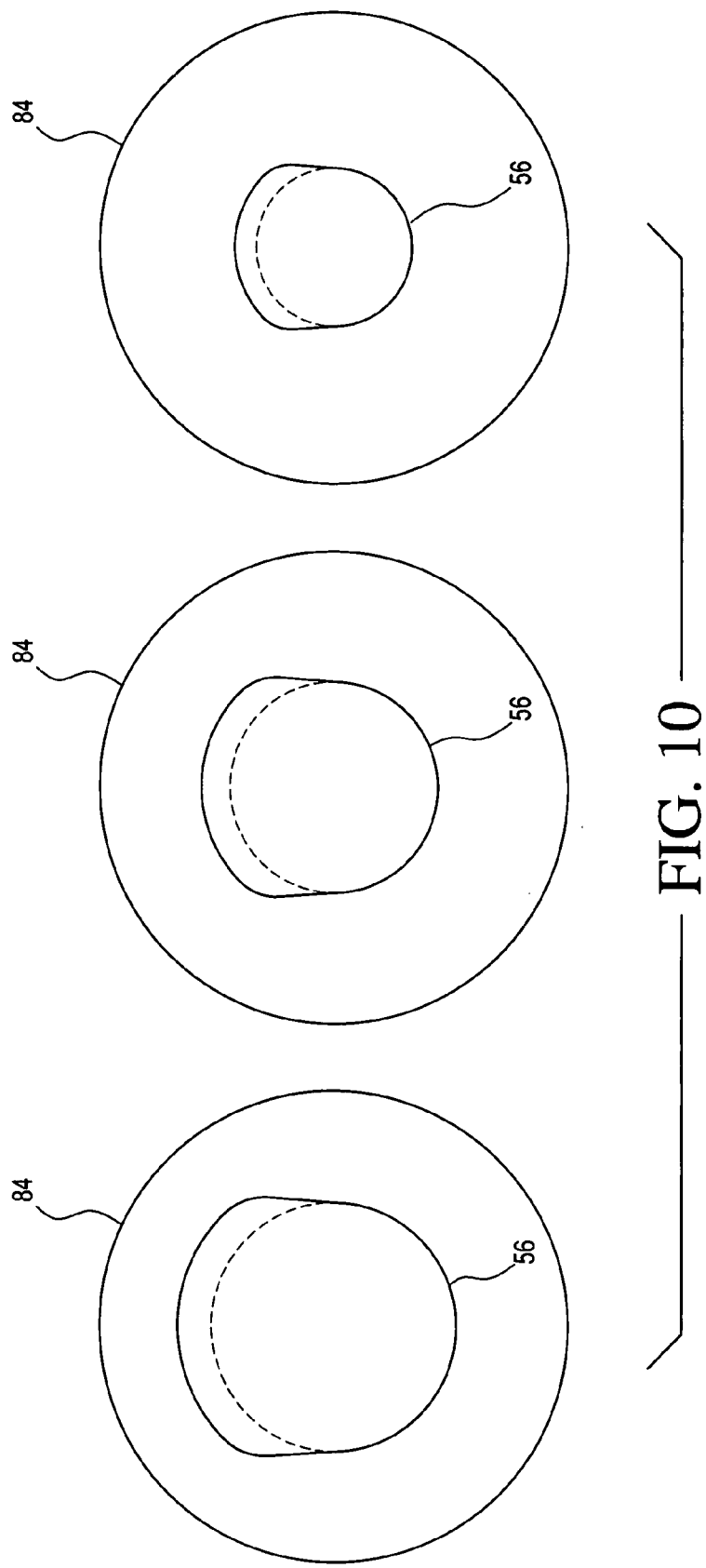
FIG. 10 shows a plurality of centering disks, each one having a different sized scanning aperture.

The scanning aperture 56 can be built into the tabletop 6. However, it is preferable to implement the aperture 56 with a removable centering disk 84 which fits into a cooperating recess 86 in the tabletop 6, as best shown in FIGS. 8 and 9. The tabletop 6 has an opening 88 which is smaller than the outside diameter of the disk 84, thereby providing a flange portion 87 to support the disk. The disk 84 preferably has a circular outer shape. Since the disk 84 is removable, several disks may be provided, each disk having a different size aperture shape, so that the proper size aperture can be chosen that best fits a particular patient, as generally shown in FIG. 10.

Although a specific shape has been disclosed for the aperture, other shapes could be employed, such as ellipses, ovals, race-track shapes, etc and disposed asymmetrically with respect to the axis of rotation 30. The peripheral edge portion 90 of the scanning aperture 56 can be made pliable to better accommodate the patient.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A patient support structure in combination with a laser imaging apparatus, including a laser scanning mechanism, comprising:
   a) a tabletop to support a female patient in front-down, prone position;
   b) said tabletop including an opening adapted to permit a breast of the patient to be vertically pendant below said tabletop;
   c) said opening being non-symmetric with respect to a vertical axis of rotation of said laser scanning mechanism disposed below said tabletop, said vertical axis projecting through said opening;
   d) said opening including a first portion defined by one side of a line across said opening through said axis and a first peripheral portion of said opening extending from said one side of said line toward the patient's feet;
   e) said opening including a second portion defined by an opposite side of said line and a second peripheral portion of said opening extending from said opposite side of said line toward the patient's head; and
   f) said second portion is elongated toward the head as compared to said first portion.

2. A patient support structure as in claim 1, wherein:
   a) the peripheral edge portion of said opening is pliable.

3. A patient support structure as in claim 1, wherein:
   a) said first portion is semi-circular defined by a first radius having a center at said axis; and
   b) said second portion is partly defined by a circular arc having a second radius greater than said first radius and having a center at said axis.

4. A patient support structure as in claim 3, wherein:
   a) said semi-circle is joined to said circular arc with a pair of tangent lines.

5. A patient support structure as in claim 1, wherein:
   a) said opening is built into said tabletop.

6. A patient support structure as in claim 1, wherein:
   a) said opening is oval.

7. A patient support structure as in claim 1, wherein:
   a) said opening is elliptical.

8. A patient support structure as in claim 1, wherein:
   a) said opening is disposed in a removable disk; and
   b) said disk is received in a pocket having a larger opening on said tabletop.

9. A patient support structure as in claim 1, wherein:
   a) said laser scanning mechanism comprises a detector array including a laser beam directed toward the breast; and
   b) said detector array being disposed below said tabletop to image the internal structure of the breast, said detector array being rotatable about said vertical axis disposed through said opening.

10. A patient support structure as in claim 9, wherein said laser source is a semiconductor diode laser.

11. A patient support structure as in claim 9, wherein said laser source is a solid state laser.

12. A patient support structure as in claim 9, wherein said laser source is a near infrared light source.

13. A patient support structure as in claim 9, wherein said detector array includes a plurality of collimators associated with respective detectors, said collimators are directed toward said axis of rotation.

14. A patient support structure as in claim 13, wherein each of said collimators includes a channel having a lens.

15. A patient support structure as in claim 13, wherein said each of said detectors is disposed at a far end of an associated collimator.

16. A patient support structure as in claim 13, wherein said detectors are photodiodes.

17. A patient support structure as in claim 13, wherein said detectors are avalanche photodiodes.

18. A patient support structure as in claim 13, wherein said detectors are phototransistors.

19. A patient support structure as in claim 13, wherein said detectors are photo multiplier tubes.

20. A patient support structure as in claim 13, wherein said detectors are microchannel plates.

* * * * *